(12) United States Patent
Romero et al.

(10) Patent No.: US 6,410,787 B2
(45) Date of Patent: Jun. 25, 2002

(54) PROCESS TO PREPARE 2-AMINOINDAN DERIVATIVES

(75) Inventors: Arthur Glenn Romero, Kalamazoo; Thomas Andrew Runge, Scotts; Bradley D. Hewitt, Kalamazoo; Kjell Anders Ivan Svensson; Chiu-Hong Lin, both of Portage; Kerry Anne Cleek, Kalamazoo; Susanne R. Haadsma-Svensson, Portage, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/783,649

(22) Filed: Feb. 14, 2001

Related U.S. Application Data

(60) Provisional application No. 60/184,020, filed on Feb. 22, 2000.

(51) Int. Cl.⁷ ..................... C07C 233/65; C07C 231/18; A61K 31/165
(52) U.S. Cl. ..................... 564/165; 564/163; 564/164; 514/619
(58) Field of Search ................................ 564/163, 164, 564/165; 514/619

(56) References Cited

U.S. PATENT DOCUMENTS

| | | | |
|---|---|---|---|
| 5,708,018 A | | 1/1998 | Haadsma-Svensson et al. ............ 514/408 |
| 6,084,130 A | * | 7/2000 | Romero et al. ............ 564/163 |

FOREIGN PATENT DOCUMENTS

| | | | |
|---|---|---|---|
| WO | WO95/04713 | 2/1995 | ......... C07C/211/42 |
| WO | WO97/45403 | 12/1997 | ......... C07C/311/05 |

OTHER PUBLICATIONS

Stjernloef P Et Al: "Structure–activity relationships in the 8–amino–6,7,8,9–Tetrahydro–3H–Benzueindole ring system. 1. Effects of substituents in the aromatic system on serotonin and dopamine receptor subtypes" Journal of Medicicinal chemistry, US, American Chemical Society. Whaington, vol. 38, No. 12, 1995 pp. 2202–2216, XP002036487.

Murray P J Et Al: "Novel 6–substituted 2–aminotetralins with potent and selective affinity for the dopamine D3 Receptor" Bioorganic & Medicinal Chemistry Letters, Oxford, GB, vol. 6, No. 4, Feb. 20. 1996 pp. 403–408 XP004135045.

* cited by examiner

*Primary Examiner*—Shailendra Kumar
(74) *Attorney, Agent, or Firm*—Lucy X. Yang; John H. Engelmann

(57) ABSTRACT

The present invention relates to (2S)-enantiomers of 2-aminoindan derivatives of formula I:

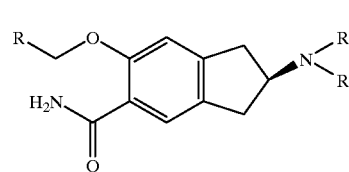

and a novel process for the preparation of them.

12 Claims, No Drawings

PROCESS TO PREPARE 2-AMINOINDAN DERIVATIVES

CROSS REFERENCE RELATED TO APPLICATION

This application claims the benefit of the following provisional application: U.S. Ser. No. 60/184,020, filed Feb. 22, 2000, under 35 USC 119(e)(i).

FIELD OF THE INVENTION

The present invention relates to (2S)-enantiomers of 2-aminoindan derivatives and a novel process for the preparation of them.

BACKGROUND OF THE INVENTION

Schizophrenia is a common and devastating mental disorder which is currently an unmet medical need. It is characterized by so-called positive (hallucinations, delusions) and negative (blunted affect, poverty of speech, social & emotional withdrawal) symptoms, as well as cognitive deficits (working memory impairment). About 1% of the world population is affected, men and women equally, with typical onset between ages 15 and 25. Antagonists of the neurotransmitter dopamine are known to block psychosis. The present invention provides compounds of formula I (wherein each R is independently $C_{1-8}$ alkyl), a highly selective $D_3$ receptor antagonist, for the treatment of Schizophrenia and other CNS diseases.

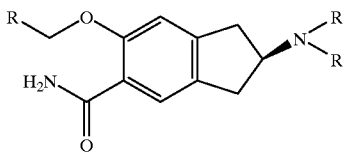

I

Racemic forms of formula I and their preparations have been disclosed in PCT publication WO 97/45403. The present invention has discovered that the (2S)-enantiomer of formula I is the form that possesses the superior desirable bioactivity. The present invention also provides a process for the synthesis, in a large scale, of said (2S)-enantiomer in a highly enantiomerically enriched form, which solved an extremely challenging problem of a long period of time.

INFORMATION DISCLOSURE

PCT International Publication No. WO 97/45403 discloses aryl substituted cyclic amines as selective dopamine D3 ligands.

U.S. Pat. No. 5,708,018 discloses 2-aminoindans as selective dopamine D3 ligands.

SUMMARY OF THE INVENTION

The present invention provides compounds of formula I:

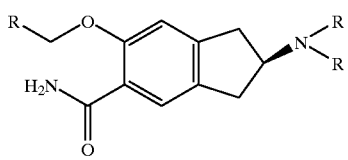

I or a pharmaceutically acceptable salt thereof wherein each R is independently $C_{1-8}$ alkyl.

More preferably, a compound of formula I of the present invention is (2S)-(+)-2-(dipropylamino)-6-ethoxy-2,3-dihydro-1H-indene-5-carboxamide or a pharmaceutically acceptable salt thereof.

In another aspect, the present invention also provides:

a process for the preparation of (2S)-enantiomers of formulas I in a highly enantiomerically enriched form;

novel intermediates in a highly enantiomerically enriched form useful for preparing compounds of formula I;

a pharmaceutical composition comprising a compound of formula I, or a pharmaceutically acceptable salt thereof, and a pharmaceutically acceptable carrier (the composition preferably comprises a therapeutically effective amount of the compound or salt), a method for treating a disease or condition in a mammal wherein a $D_3$ receptor is implicated and modulation of a $D_3$ receptor function is desired comprising administering a therapeutically effective amount of a compound of formula I, or a pharmaceutically acceptable salt thereof to the mammal;

a method for treating or preventing anxiety, obesity, depression, schizophrenia, a stress related disease (e.g. general anxiety disorder), panic disorder, sleep disorders, a phobia, mania, obsessive compulsive disorder, post-traumatic-stress syndrome, immune system depression, a stress induced problem with the gastrointestinal or cardiovascular system, or sexual dysfunction in a mammal comprising administering a therapeutically effective amount of a compound of formula I, or a pharmaceutically acceptable salt thereof to the mammal;

a method for treating or preventing ADHD (attention deficit hyperactivity disorder), migraine, substance abuse (including smoking cessation), cognitive deficits, memory impairment, alzheimer's disease, movement disorders including choreatic movements in huntington's disease or motor complications such as dystonias and dyskinesias in Parkinson's disease, extrapyramidal side effects related to the use of neuroleptics, and "Tics" including Tourette's syndrome in a mammal comprising administering a therapeutically effective amount of a compound of formula I, or a pharmaceutically acceptable salt thereof to the mammal.

DETAILED DESCRIPTION OF THE INVENTION

The following definitions are used, unless otherwise described.

The term alkyl refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-8}$ alkyl refers to alkyl of one to eight carbon atoms, inclusive.

Mammal refers to human or animals.

Pharmaceutically acceptable salts refer to organic acid addition salts such as tosylate, methanesulfonate, acetate, citrate, malonate, tartarate, succinate, benzoate, ascorbate, α-ketoglutarate, α-glycerophosphate, or suitable inorganic salts including hydrochloride, hydrobromide, sulfate, nitrate, bicarbonate, and carbonate salts, etc.

The term "chiral salt" refers to a salt containing a chiral acid. The term "chiral acids" refers to the acids having one or more chiral centers. Examples of chiral acids are tartaric acid, di-benzoyltartaric acid, di-para-toluoyltartaric acid, camphorsulfonic acid, and mandelic acid. The preferred chiral acid is mandelic acid.

All temperatures are in degrees Centigrade.

$[α]_D 25$ refers to the angle of rotation of plane polarized light (specific optical rotation) at 25° C. with the sodium D line (589 A).

The compounds of formula I are active orally or parenterally. Orally the formula I compounds can be given in solid dosage forms such as tablets or capsules, or can be given in liquid dosage forms such as elixirs, syrups or suspensions as is known to those skilled in the art. It is preferred that the formula I compounds be given in solid dosage form and that it be a tablet.

Typically, the compounds of formula I can be given in the amount of about 0.5 mg to about 250 mg/person, one to three times a day. Preferably, about 5 to about 50 mg/day in divided doses.

The exact dosage and frequency of administration depends on the particular compound of formula I used, the particular condition being treated, the severity of the condition being treated, the age, weight, general physical condition of the particular patient, other medication the individual may be taking as is well known to those skilled in the art and can be more accurately determined by measuring the blood level or concentration of the active compound in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar pharmaceutical diluent or carrier materials. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

The present invention provides a process for preparing compounds of formula I in a highly enantiomerically enriched form as depicted in Scheme I. The starting material I-1 in Scheme I can be prepared according to the procedures described in Chart A of U.S. Pat. No. 5,708,018.

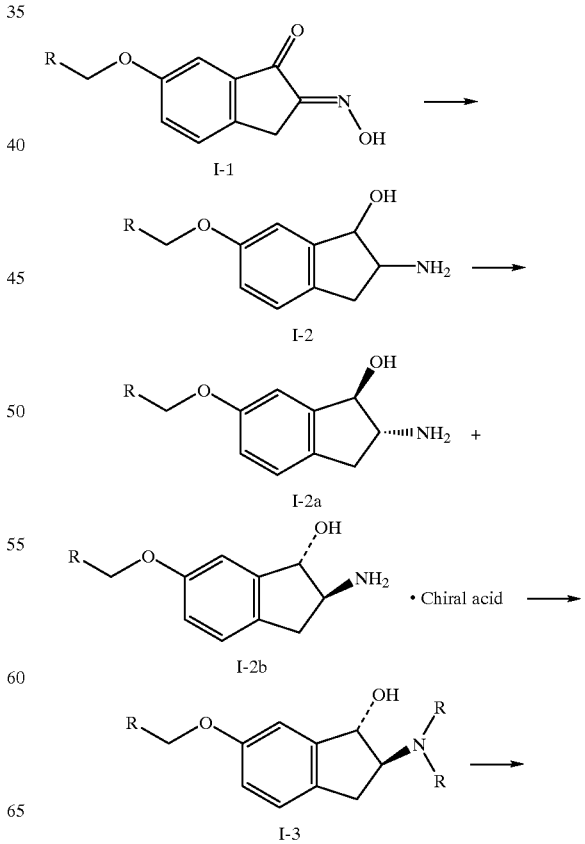

SCHEME I

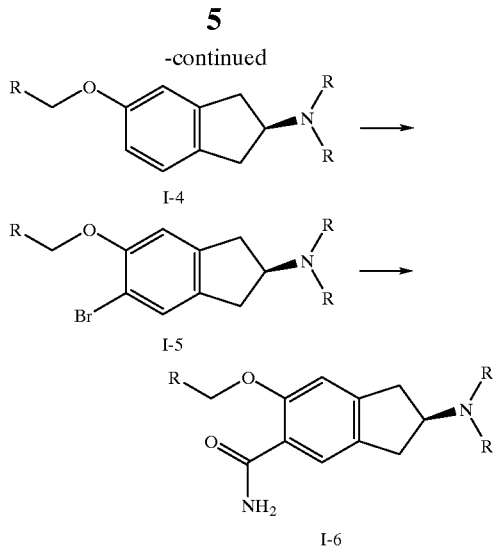

In step 1, compound I-1 is converted to compound I-2 as a racemic mixture via catalytic hydrogenation in the presence of an appropriate catalyst, such as palladium on carbon, W-2 Raney nickel or platinum on sulfide carbon, in an appropriate solvent, such as ethanol, THF, ethyl acetate or combinations thereof. The desired enantiomer I-2b can be obtained by treating structure I-2 with an appropriate chiral acid in an appropriate solvent to form the corresponding chiral salt complex, which subsequently crystallizes from the solvent. Resolutions to separate an individual enantiomer I-2a or I-2b from a racemic mixture often pose a significant challenge in the quest to obtain enantiomerically pure compound. In general, a wide variety of enantiomerically pure acids can provide some measure of enantiomer enrichment. However, the choice of the particular chiral acid and solvent system proves very important to the efficiency of the resolution (enantiomeric purity and chemical yield). The preferred chiral acids in the present invention for the resolution include tartaric acid, di-benzoyltartaric acid, di-para-toluoyltartaric acid, camphorsulfonic acid, and mandelic acid. The most preferred chiral acid is mandelic acid. An examination of resolving acids and solvent systems indicate that (R)-(−)-mandelic acid and (1R)-(−)-10-camphorsulfonic acid perform very well for the resolution of racemic I-2 to induce the crystallization of almost enantiomerically pure I-2b, with (R)-(−)mandelic acid being preferred. Note that it is not necessary to obtain enantiomer I-2b as 100% pure enantiomeric material at this stage of the synthesis since subsequent crystallization procedures in the following procedures will serve to provide a slight upgrade to the final enantiomeric purity. It will be apparent to those skilled in the art that other chiral acids commonly used to perform resolution of amines may also be useful for this resolution. Solvent systems in the present invention, which are found to be useful to optimize the recovery of compound I-2b, include alcohol solvents such as methanol, ethanol, isopropanol, etc. as well as co-solvents of alcohol(s), acetonitrile (ACN), or water in various proportions such as tetrahydrofuran (THF), ether, methyl tertiary butyl ether (MTBE), dimethoxyethane (DME), etc. The preferred solvent system in combination with (R)-(−)-mandelic acid is a mixture of methanol and tetrahydrofuran.

Next, alkylation of I-2b, in a form of free base or chiral salt complex, with an alkylation agent in the presence of an appropriate base and an appropriate polar solvent system at a temperature in a range of about 20° C. to 90° C. provides compound I-3. The appropriate base includes $K_2CO_3$, $Na_3PO_4$, $Na_2B_4O_7$, etc. The preferred base is $Na_3PO_4$. The appropriate solvent includes ACN, dimethylformamide (DMF), or THF. The preferred solvent is ACN. The preferred temperature is in a range of from about 60° C. to about 75° C. Compound I-3 is then converted to compound I-4 by acetylation followed by hydrogenolysis in the presence of an appropriate catalyst, such as palladium on carbon or platinum on sulfide carbon, and an appropriate acetylation reagent such as acetic anhydride, or acetyl chloride with catalytic dimethylaminopyridine, in an appropriate solvent, such as acetic acid, an alcohol, water or combinations thereof, at a temperature in a range of from about 20° C. to reflux. The preferred condition for this reaction is in acetic anhydride/acetic acid at a temperature in a range of from about 55° C. to about 70° C. Bromination of compound I-4 with a brominating reagent in the presence of an acid and a polar solvent system at a temperature in a range of from about −78° C. to about room temperature provides compound I-5. The instant bromination provides an unexpected improvement in regioselectivity for bromination at the desired position by using an appropriate brominating reagent. A suitable brominating reagent may be $Br_2$, dibromantin, N-bromosuccinimide (NBS), pyridinium tribromide (pyrHBr$_3$). The preferred brominating reagent is pyridinium tribromide. The acid in the reaction is preferably a strong acid such as HBr, $H_2SO_4$, $TiCl_4$, TFA, $MeSO_3H$, $Cl_3CCO_2H$, $Cl_2CCO_2H$, or citric acid. The more preferred acid is TFA. The suitable polar solvent may be ACN, DMF, EtOAc, an alcohol such as methanol, $CH_2Cl_2$, MTBE, THF, etc. The preferred solvent is $CH_2Cl_2$. The preferred temperature is in a range from about −15° C. to room temperature. Finally, carboxamidation I-5 in the presence of transition metal such as palladium, palladium on carbon or palladium acetate and associated ligands such as mono or bidentate phosphines in an appropriate solvent with an appropriate base at a temperature in a range from about 70° C. to about 140° C. provides the desired compound I-6. Preferred ligands include triphenylphosphine, tri-orthotolulyphosphine, or 1,3-bis(diphenylphosphino)propane. Preferred temperature is in a range from about 95° C. to about 105° C. The appropriate solvents include dimethylformamide, dioxane, toluene, dimethoxyethane, dimetylacetamide, etc. The preferred solvent is dimethylformamide. The appropriate base include potassium carbonate, tertiary amine bases, $Na_3PO_4$, LiHMDS, Li-amides, alkoxides, etc. The preferred base is potassium carbonate.

Without further elaboration, it is believe that one skilled in the art can, using the preceding description, practice the present invention to its fullest extent. The following detailed example describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE

Preparation of (2S)-(+)-2-(Dipropylamino)-6-ethoxy-2,3-dihydro-1H-indene-5-carboxamide

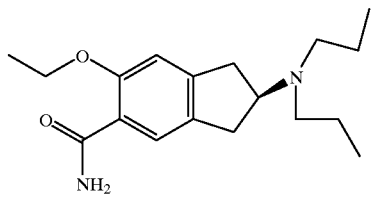

Step 1: Preparation of 4-ethoxycinamic acid

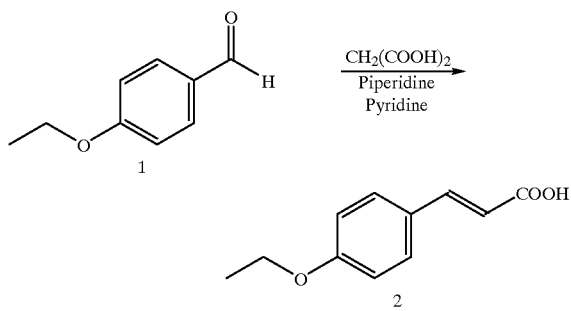

4-Ethoxybenzaldehyde (1) is condensed with malonic acid in the presence of base (Knovenagel reaction) to obtain the cinnamic acid derivative 2. This is accomplished by dissolving 1 in pyridine with 0.15 eq. of piperidine and heating the resulting solution to 50– 135° C. (preferably 105–125° C.) after which a solution of malonic acid (2 eq.) dissolved in pyridine is added in a slow stream. Approximately 40% of the pyridine is slowly distilled off and the heating continued at 125° C. until TLC indicated that all of 1 has been consumed. Cool to 40° C. and add excess concentrated hydrochloric acid, keeping the temperature at around 40° C. Cool to below room temperature and filter the solid product (2), washing with water and then drying.

$^1$H NMR (300 MHz, CDCl$_3$) δ1.43 (t, J=7.0 Hz, 3 H), 4.07 (q, J=7.0 Hz, 2 H), 6.31 (d, J=16.0 Hz, 1 H), 6.90 (d, J=8.8 Hz, 2 H), 7.49 (d, J=8.7 Hz, 2 H), 7.74 (d, J=15.9 Hz, 1 H).

Step 2: Preparation of 4-ethoxycinnamic acid

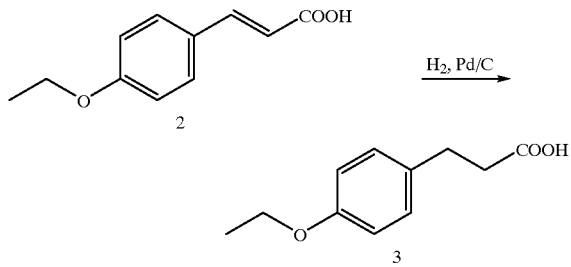

4-Ethoxycinnamic acid (2) is hydrogenated at 40 p.s.i. with catalytic 5% palladium on carbon in tetrahydrofuran solvent to obtain 3-(4-ethoxyphenyl)propionic acid (3). A sample is recrystallized from ethyl acetate/hexane to obtain an analytically pure sample (m.p. 101–103° C.).

$^1$H NMR (300 MHz, CDCl$_3$) δ1.40 (t, J=7.0 Hz, 3 H), 2.65 (t, J=7.7 Hz, 2 H), 2.90 (t, J=7.7Hz, 2 H), 4.01 (q, J=7.0 Hz, 2 H), 6.83 (d, J=8.6 Hz, 2 H), 7.12 (d, J=8.6 Hz,2 H).

Step 3: Preparation of 6-ethoxy-1-indanone

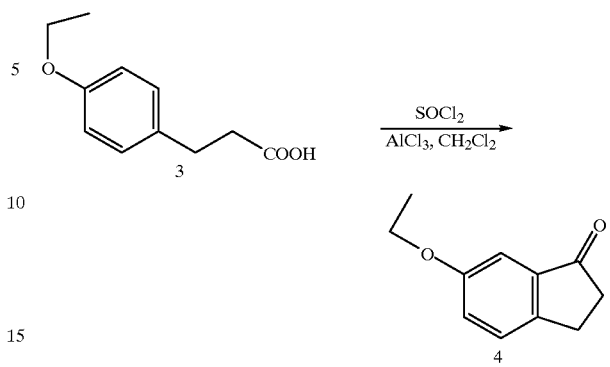

To carboxylic acid 3 is added thionyl chloride (2 eq.) and catalytic dimethylformamide. The solution is stirred until analysis indicated that all of the carboxylic acid had been converted to the acid chloride. Remove volatile reagents under vacuum. The acid chloride is dissolved in dichloromethane and added to a slurry of aluminum chloride (1.1 eq.) in dichloromethane over 15–60 minutes. The resulting mixture is heated to reflux for 30 minutes (until analysis indicated that all of the starting material had been consumed) and then cooled to 0–15° C. Water is added slowly to quench the reaction and then the mixture is extracted. The organic layer is washed with saturated aqueous sodium bicarbonate and the organic solution is stripped of dichloromethane solvent under vacuum to afford a residue that is redissolved in methyl t-butyl ether and then dried with magnesium sulfate. The solution is filtered and the solvent removed under vacuum to afford solid 4. The solid could be recrystallized from octane to afford an analytical sample (m.p. 57–58° C.).

$^1$H NMR (300 MHz, CDCl$_3$) δ1.41 (t, J=7.0 Hz, 3 H), 2.66–2.71 (m, 2 H), 3.04 (t, J=5.7 Hz, 2 H), 4.04 (q, J=7.0 Hz, 2 H), 7.13–7.18 (m, 2 H), 7.32–7.35 (m, 1 H).

Step 4: Preparation of 6-ethoxy-1H-indene-1,2(3H)-dione-2-oxime

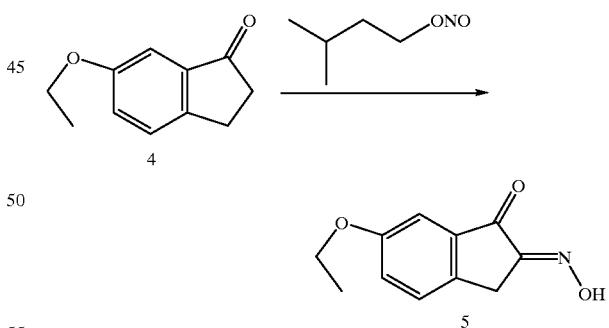

A solution of 6-ethoxy-1-indanone and isoamylnitrite (1.5 eq.) in ethyl acetate arecooled to approximately 0° C. and concentrated hydrochloric acid (1.1 acid equivalents) is added at a rate to keep the temperature below 40° C. After the addition is completed the slurry is stirred at 5–10° C. until analysis indicated that all of the starting material is consumed. The product is filtered and rinsed with cold ethyl acetate. The oxime product (5) can be easily purified by refluxing as a slurry in anhydrous ethanol, cooling filtering, and then washing the solid with more ethanol and then drying (m.p. 220° C. decomp.).

$^1$H NMR (300 MHz, DMSO-d$_6$) δ1.32 (t, J=7.0 Hz, 3 H), 3.65 (s, 2 H), 4.06 (q, J=7.0 Hz, 2 H), 7.14 (d, J=2.5 Hz, 1 H), 7.27 (dd, J=2.6, 8.4 Hz, 1 H), 7.49 (d, J=8.4 Hz, 1 H), 12.57 (s, 1 H).

Step 5: Preparation of (±)-trans-2-amino-6-ethoxy-2,3-dihydro-1H-inden-1-ol

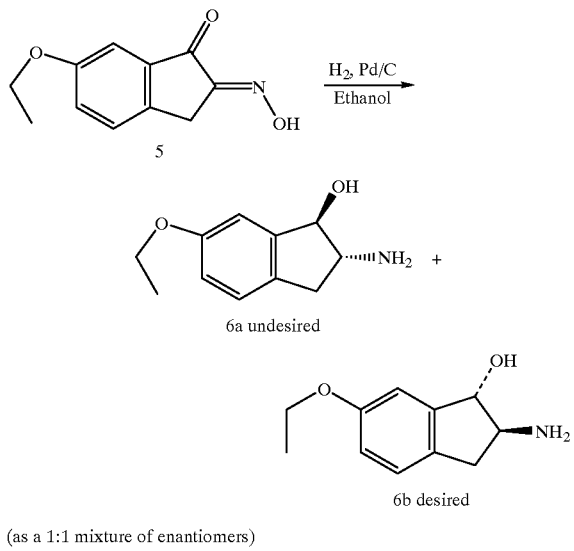

(as a 1:1 mixture of enantiomers)

6-Ethoxy-1H-indene-1,2(3H)-dione 2-oxime is slurried in absolute ethanol, and approximately 0.5 eq. 2N sodium hydroxide is added. Palladium on carbon is added, and the mixture is hydrogenated in a Parr shaker with an initial hydrogen pressure of 40 psi for several hours (depending upon the scale of the reaction and the catalyst loading). After analysis indicated that all of the starting material is consumed, the catalyst is filtered from the solution and then the solvent is removed under vacuum, and the residue is diluted with water and extracted with ethyl acetate several times. The ethyl acetate extracts are combined and concentrated under vacuum. Hexane is added and the resulting slurry is cooled to 0–15° C. and the solid product (6) is rinsed with cold ethyl acetate/hexane (1:1). The product is dried under vacuum.

An analytical sample is obtained by combined an aliquot of the product (6) with p-toluene sulfonic acid, and the resulting salt is crystallized from methanol/diethylether to afford a material of m.p. 172–173° C.

$^1$H NMR (300 MHz, CDCl$_3$) δ1.394 (t, J=7.0 Hz, 3 H), 2.51 (dd, J=8.3, 14.9 Hz, 1 H), 3.13 (dd, J=7.3, 15.1 Hz, 1 H), 3.43 (q, J=7.2 Hz, 1 H), 4.02 (q, J=7.0 Hz, 2 H), 4.73 (d, J=6.7 Hz, 1 H), 6.78 (dd, J=2.2, 8.2 Hz, 1 H), 6.90 (d, J=2.2 Hz, 1 H), 7.06 (d, J=8.2 Hz, 1 H).

Step 6: Preparation of (1S, 2S)-trans-(−)-2-amino-6-ethoxy-2,3-dihydro-1H-inden-1-ol (R)-(−)-mandelate

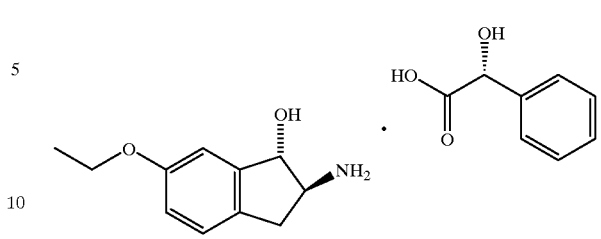

(±)-trans-2-Amino-6-ethoxy-2,3-dihydro-1H-inden-1-ol in a mixture of methanol and tetrahydrofuran is added to a warm solution of a slight molar excess of (R)-(−)-mandelic acid in tetrahydrofuran, so that the result is a solution at about 60° C. in about 3–4 ml/g methanol and about 40–50 ml/g tetrahydrofuran. The desired mandelate salt (7) crystallizes from solution and is isolated by filtration and drying. (m.p. 170–195° C.). When treated with (R)-(−)-10-camphorsulfonic acid in methanol, the desired enantiomer (7) crystallizes from solution as the sulfonic acid salt complex (m.p. 238–239° C.). [α]$^{25}$D=−8° (c=0.94, methanol).

Step 7: Preparation of (1S, 2S)-trans-2-(dipropylamino)-6-ethoxy-2,3-dihydro-1H-inden-1-ol

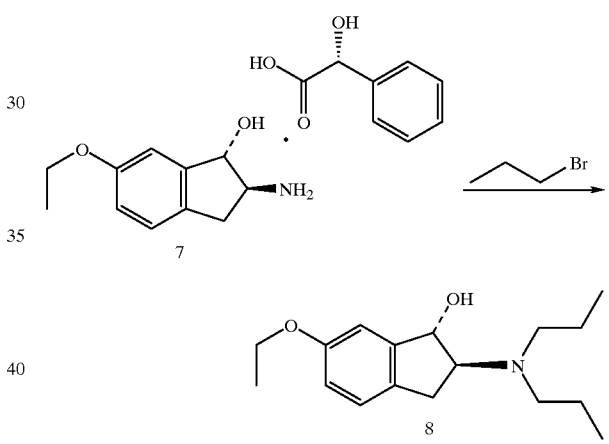

Aminoalcohol mandelate salt (7) is added to acetonitrile solvent with excess tribasic sodium phosphate and n-bromopropane and stirred until analysis indicates that starting material is completely converted to the dipropyl-substituted material (8). The preferred procedure is to heat the slurry at 60–70° C. for two—three days. The reaction is cooled, filtered, and the solids rinsed with methyl t-butyl ether. The solution is concentrated under vacuum and then more methyl t-butyl ether is added and the solution extracted with aqueous sodium hydroxide. The organic layer is washed with excess dilute aqueous hydrochloric acid and the aqueous hydrochloric acid extracts are combined and back-washed with methyl t-butyl ether and then made basic with concentrated aqueous sodium hydroxide. This aqueous solution is then washed with methyl t-butyl ether. The ether is removed under vacuum to obtain the dipropyl compound (8) as a solid. It is apparent to those skilled in the art that other similar alkylating reagents can be utilized in place of n-bromopropane, such as n-propyliodide, etc. Also, other bases can be utilized in place of the phosphate base, such as sodium carbonate, organic tertiary amine bases such as diisopropylethylamine, etc. The preferred procedure is to use n-bromopropane and tribasic sodium phosphate.

Additionally, it is apparent to those skilled in the art that reductive amination procedures can also be used to perform this chemical transformation, including using propanal in the presence of a hydride transfer reducing reagent such as sodium triacetoxyborohydride, sodium cyanoborohydride, etc. Alternatively, the amine can be repetitively acylated to form the propionamide of the amine and then reduced to the amine with lithium aluminum hydride, diisobutylhydride, a borane reagent, etc. two times to introduce the required propyl groups. The preferred method to obtain 8 is to heat 7 with n-bromopropane in the presence of tribasic sodium phosphate. An analytical sample can be crystallized from ethyl acetate/hexane (m.p. 74–75° C.).

$^1$H NMR (300 MHz, CDCl$_3$) δ0.90 (t, J=7.4 Hz, 6 H), 1.40 (t, J=7.0 Hz, 3 H), 1.52 (sextet, J=7.3 Hz, 4 H), 2.38 (br.s, 1 H), 2.47–2.64 (m, 4 H), 2.72 (dd, J=9.1, 15.1 Hz, 1 H), 2.89 (dd, J=7.8, 15.1 Hz, 1 H), 3.41 (dd, J=7.7, 16.6 Hz, 1 H), 4.02 (q, J=7.0 Hz, 2 H), 5.07 (d, J=7.4 Hz, 1 H), 6.78 (dd, J=2.4, 8.2 Hz, 1 H), 6.92 (d, J=2.2 Hz, 1 H), 7.06 (d, J=8.2 Hz, 1 H); [α]$^{25}$D=34° (c=1.01, methanol).

Step 8: Preparation of (S)-5-ethoxy-2,3-dihydro-N,N-dipropyl-1H-inden-2-amine

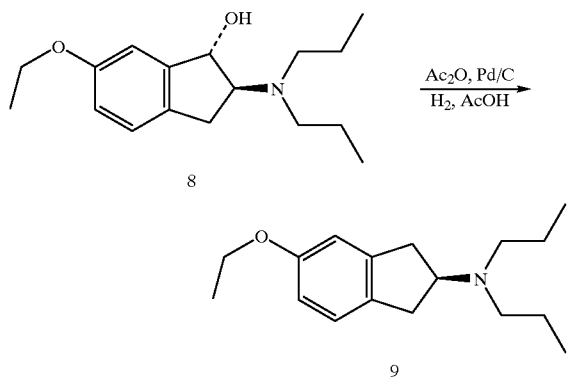

(1S)-Trans-2-(dipropylamino)-6-ethoxy-2,3-dihydro-1H-inden-1-ol 8 is placed into a hydrogenation reactor with a catalytic amount of 5% palladium on carbon and acetic acid added as solvent. Acetic anhydride (excess over one equivalent—sufficient to completely convert all of 8 to the unisolated acetate intermediate) is also added and the mixture is hydrogenated at 40 p.s.i. while heating to 25°–80° C. (preferred temperature is 60°–70° C. When analysis indicated that 8 had been completely converted into 9 the mixture is cooled and filtered. The solvent is removed by heating under vacuum and the residue is extracted with methyl t-butyl ether and aqueous sodium hydroxide (added until the solution indicated a pH greater than 12). The aqueous layer is back extracted with more methyl t-butyl ether and the combined organic layers are washed with dilute aqueous sodium hydroxide solution. The methyl t-butyl ether solution is then extracted twice with 1 N aqueous hydrochloric acid, adding sufficient acid to wash all of the amine product into the aqueous layer). The aqueous acid layers are combined and washed with methyl t-butyl ether after which the aqueous layer is adjusted to a pH greater than 12 and then extracted with two portions of dichloromethane. The dichloromethane is washed with water and the solvent removed by heating under vacuum to afford 9. An analytical sample can be prepared as the p-toluenesulfonic acid salt from methanol/diethylether to afford crystals (m.p. 136–138° C.).

$^1$H NMR (free base, 300 MHz, CDCl$_3$) δ0.88 (t, J=7.3 Hz, 6 H), 1.39 (t, J=7.0 Hz, 2 H), 1.49 (sextet, J=7.5 Hz, 4 H), 2.46–2.51 (m, 4 H), 2.75–3.01 (m, 4 H), 3.64 (quintet, J=8.2 Hz, 1 H), 3.99 (q, J=7.0 Hz, 2 H), 6.68 (d, J=8.2 Hz, 1 H), 6.73 (s, 1 H), 7.05 (d, J=8.1 Hz, 1 H); [α]$^{25}$D=11°(c=0.82, methanol).

Step 9: Preparation of (R)-5-bromo-6-ethoxy-2,3-dihydro-N,N-dipropyl-1H-inden-2-amine

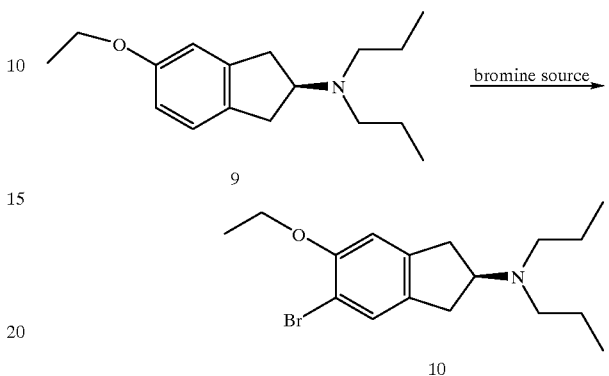

Pyridinium perbromide 1–1.5 equivalents (preferably 1.3–1.4 equivalents) is added to dichloromethane solvent and cooled between –60° C. and 25° C. (–15° C. to 25° C. is the preferred temperature range). A –15° C. solution of (S)-6-ethoxy-2,3-dihydro-N,N-dipropyl-1H-inden-2-amine (9) and trifluoroacetic acid (1–5 equivalents with 3 equivalents being preferred) dissolved in dichloromethane is added. After stirring for several hours the reaction is warmed to 0° C. When analysis indicated that all of 9 had been consumed, the reaction is quenched with a reducing agent such as aqueous sodium bisulfite. Aqueous sodium hydroxide is then added to make the pH greater than 12 and most of the dichloromethane and pyridine are removed by heating under vacuum. The residue is extracted several times with methyl t-butyl ether, the organic layers are combined, stirred with magnesium sulfate to dry, filtered, and the solvent removed by heating under vacuum to afford 10 in crude form. If necessary, this is crystallized from methanol/methyl t-butyl ether as the hydrochloride salt to afford purified 10 as its hydrochloride salt (m.p. of an analytical sample 202–204° C.).

It will be apparent to one skilled in the art that other methods of brominating 9 exist, such as direct treatment with bromine, N-bromosuccinimide, dibromohydantoin, etc. Other acid catalysts can also be utilized, such as acetic acid and other low molecular weight carboxylic acids, mineral acids, organic sulfonic acids, etc. Trifluoroacetic acid is the preferred acid catalyst.

$^1$H NMR (free base, 300 MHz, CDCl$_3$) δ0.86 (t, J=7.4 Hz, 6 H), 1.41 –1.55 (m, 7 H), 2.43–2.49 (m, 4 H), 2.76–2.99 (m, 4 H), 3.57 (quintet, J=8.2 Hz, 1 H), 4.05 (q, J=7.0 Hz, 2 H), 6.73 (s, 1 H), 7.31 (s, 1 H); [α]$^{25}$D=5°(c=1.01, methanol).

Step 10: Preparation of (S)-(+)-(dipropylamino)-6-ethoxy-2,3-dihydro-1H-indene-5-carboxamide

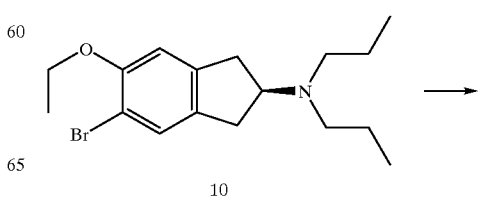

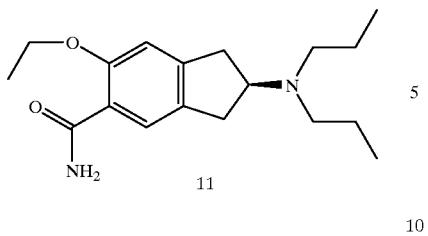

Compound 10 (as its hydrochloride salt) is combined with dimethylformamide with a catalytic amount of palladium acetate (0.008–0.08 equiv., with 0.01–0.04 equiv. being preferred) and 1,3-bis(diphenylphosphino)propane (approximately twice the number of molar equivalents as the palladium catalyst), potassium carbonate, and hexamethyldisilylazane. The reaction is heated to 70°–120° C. (100° C. being preferred) under an atmosphere of carbon monoxide until analysis indicated that all of 10 had been consumed. The reaction is cooled, diluted with methyl t-butyl ether (MTBE) and water, and filtered to remove solids. The two-phase mixture is made basic and product is extracted into MTBE. The extracts are washed with dilute base, then water. The solution is placed under vacuum and heated to remove volatile reagents and solvents. The residue is slurried with aqueous hydrochloric acid and filtered. The filtrate is extracted with MTBE. The aqueous phase is made basic with aqueous sodium hydroxide, and the product is extracted into methyl t-butyl ether. The extracts are washed again with water and then dried by distillation. The resulting MTBE solution is treated with magnesium silicate adsorbent, which is removed by filtration. The methyl t-butyl ether filtrate is concentrated and heptane added at approximately 50° C. followed by gradual cooling to induce the crystallization of 11 which is filtered and dried. It is readily apparent to one skilled in the art that a variety of palladium catalysts ($PdCl_2$, $Pd_n(dba)_m$, etc.) and associated ligands (triphenylphosphine, tri-ortho-tolulyphosphine, etc) can be utilized in varying catalytic quantities.

Additionally, 10 in its free base form can be dissolved in an etheral solvent such as tetrahydrofuran and cooled to −20° to −78° C. (preferably −25° to −50° C.) and a solution of an alkyllithium such as t-butyllithium added. Trimethylsilylisocyanate (see Parker, K. A.; Gibbons, E. G. "A Direct Synthesis of Primary Amides from Grignard Reagents", Tetrahed. Lett. 1975, 981–984) is then added and the solution is allowed to slowly warm to 10° C. and then quenched by the addition of water. Methyl t-butyl ether is added and the mixture is extracted. The organic layer is dried with magnesium sulfate and the solvent removed to afford 11 which is purified as the hydrochloride salt by treating with a methanol solution of hydrochloric acid, concentrating under vacuum, and recrystallizing the solid from ethyl acetate. The crystals are converted to the freebase by treatment with aqueous sodium hydroxide, extraction into ethyl acetate, drying with magnesium sulfate, and removal of the solvent under vacuum (m.p. 100–101° C.).

$^1$H NMR ($CDCl_3$) δ7.99 (s, 1 H), 7.87 (bs, 1 H), 6.78 (s, 1 H), 6.12 (bs, 1 H), 4.17–4.11 (q, J=7.0 Hz, 2 H), 3.72–3.61 (m, 1 H), 3.06–2.78 (m, 4 H), 2.48–2.43 (m, 4 H), 1.54 –1.41 (m, 7 H), 0.87 (t, J=7.3 Hz, 6 H; $[\alpha]^{25}D$=+4.94°(c=0.842, MeOH).

We claim:

1. A compound of formula I

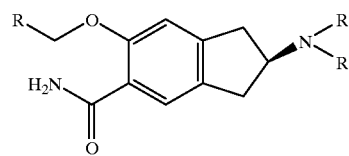

or a pharmaceutically acceptable salt thereof wherein each R is independently $C_{1-8}$ alkyl.

2. A compound of formula 1 as shown in claim I which is (2S)-(+)-2-(dipropylamino)-6-ethoxy-2,3-dihydro-1H-indene-5-carboxamide or a pharmaceutically acceptable salt thereof.

3. A process for preparing a compound of formula I

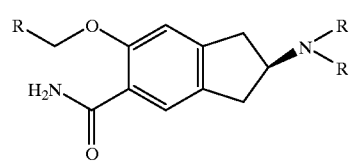

wherein each R is independently $C_{1-8}$ alkyl which comprises steps of a) hydrogenation of compound of I-1 to compound I-2 as a racemic mixture

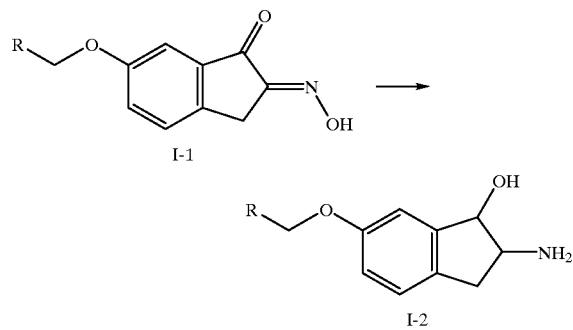

in the presence of an appropriate catalyst and an appropriate solvent;

b) resolution of compound I-2 to compound I-2b

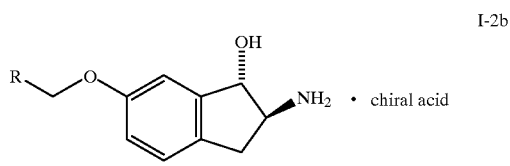

by treating compound I-2 with a chiral acid in an appropriate solvent;

c) alkylation of I-2b in the presence of a base and an appropriate solvent system to provide compound I-3;

d) converting compound I-3 to compound I-4;

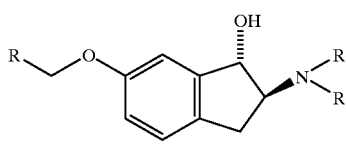

e) bromination of compound I-4 to compound I-5;

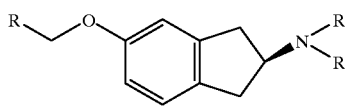

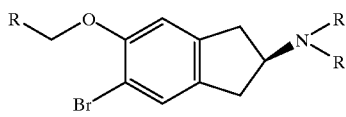

with a brominating reagent in the presence of an acid and an appropriate solvent system; and f) carboxamidation I-5 in the presence of transition metal and an associated ligand in an appropriate solvent with an appropriate base, or alternatively treating I-5 with an alkyllithium followed by trimethylsilylisocyanate, to provide a compound of formula I.

4. A process of claim 3 wherein said chiral acid is tartaric acid, di-benzoyltartaric acid, di-para-toluoyltartaric acid, camphorsulfonic acid, or mandelic acid.

5. A process of claim 3 wherein the chiral acid is (1R)-(−)-10-camphorsulfonic acid, or (R)-(−)-mandelic acid.

6. A process of claim 3 wherein said appropriate solvent system in step b) is a mixture of methanol and tetrahydrofuran.

7. A process of claim 3 wherein said brominating reagent in step d) is pyridinium tribromide.

8. A process of claim 3 wherein said transition metal in step e) is palladium, palladium on carbon or palladium acetate and said associated ligand is triphenylphosphine, tri-orthotolulyphosphine, or 1,3-bis(diphenylphosphino) propane.

9. A method for treating or preventing a central nervous system disorder associated with dopamine D3 receptor activity comprising administering to a mammal in need thereof an effective amount of formula I as shown in claim 1.

10. The method of claim 9 wherein said disorder is anxiety, obesity, depression, schizophrenia, a stress related disease, panic disorder, sleep disorders, a phobia, mania, obsessive compulsive disorder, post-traumatic-stress syndrome, immune system depression, a stress induced problem with the gastrointestinal or cardiovascular system, or sexual dysfunction.

11. The method of claim 9 wherein said disorder is attention deficit hyperactivity disorder, migraine, substance abuse, cognitive deficits, memory impairment, alzheimer's disease, movement disorders, disease, motor complications, extrapyramidal side effects related to the use of neuroleptics, or "Tics" including Tourette's syndrome.

12. The method of claim 11 wherein said substance abuse is drug abuse or smoking abuse; wherein movement disorder is choreatic movements in huntington's; wherein motor complications are dystonias and dyskinesias in Parkinson's disease.

* * * * *